(12) United States Patent
Yu et al.

(10) Patent No.: US 8,563,713 B2
(45) Date of Patent: *Oct. 22, 2013

(54) ANTIBODIES SPECIFIC TO CARBAMAZEPINE

(75) Inventors: Liuming Yu, Guangzhou (CN);
Yaoming Liang, Guangzhou (CN);
Hongbo Li, Guangzhou (CN)

(73) Assignee: Guangzhou Kingmed Center for Clinical Laboratory, Guangzhou (CN)

( * ) Notice: Subject to any disclaimer, the term of this patent is extended or adjusted under 35 U.S.C. 154(b) by 168 days.

This patent is subject to a terminal disclaimer.

(21) Appl. No.: 13/069,192

(22) Filed: Mar. 22, 2011

(65) Prior Publication Data

US 2012/0244546 A1 Sep. 27, 2012

(30) Foreign Application Priority Data

Mar. 2, 2011 (CN) .......................... 2011 1 0049828
Mar. 2, 2011 (CN) .......................... 2011 1 0049830

(51) Int. Cl.
*C07D 223/18* (2006.01)
*G01N 33/531* (2006.01)
*C07K 16/44* (2006.01)
*C07K 14/00* (2006.01)

(52) U.S. Cl.
USPC ............ 540/589; 435/7.1; 436/501; 530/350; 530/387.1; 530/389.1

(58) Field of Classification Search
None
See application file for complete search history.

(56) References Cited

U.S. PATENT DOCUMENTS

| 4,058,511 | A | * | 11/1977 | Singh | 530/363 |
| 5,395,933 | A | | 3/1995 | Ponticello et al. | 540/589 |
| 5,543,311 | A | | 8/1996 | Brummond et al. | 435/188 |
| 5,578,457 | A | | 11/1996 | Brummond et al. | 435/7.93 |
| 5,688,944 | A | | 11/1997 | Wang | 540/529 |
| 5,821,342 | A | | 10/1998 | Wang | 530/389.8 |
| 5,830,768 | A | | 11/1998 | Wang | 436/533 |
| 5,852,779 | A | | 12/1998 | Sawyer | 455/445 |
| 7,229,782 | B1 | | 6/2007 | Yu | 435/7.92 |

OTHER PUBLICATIONS

A print-out retrieved from http://www.piercenet.com/browse.cfm?fldID=F3305493-0FBC-93DA-2720-4412D198A9C9 on Feb. 1, 2013.*
Ju et al., "Detection of 2-Hydroxyiminostilbene in the Urine of Patients Taking Carbamazepine and Its Oxidation to a Reactive Iminoquinone Intermediate," J. Pharm. Exp. Ther., 1999, vol. 288, No. 1, pp. 51-56.*
Bahlmann et al., "Monitoring carbamazepine in surface and wastewaters by an immunoassay based on a monoclonal antibody," Anal. Bioanal. Chem., 2009, vol. 395, issue 6, pp. 1809-1820.*
Hollis et al., "Determination of vitamin D status by radioimmunoassay with an 125I-labeled tracer," Clin. Chem., 1993, vol. 39, pp. 529-533.*
Pearce et al., "Pathways of Carbamazepine Bioactivation in Vitro I. Characterization of Human Cytochromes P450 Responsible for the Formation of 2- and 3-Hydroxylated Metabolites," Drug Metabol. Dispos., 2002, vol. 30, No. 11, pp. 1170-1179.*
Rosowsky et al., "Synthesis of 2,4-Diamino-6-[2'-O-(ω-carboxyalkyl)oxydibenz[b,f]azepin-5-yl]methylpteridines as Potent and Selective Inhibitors of *Pneumocystis carinii, Toxoplasma gondii,* and *Mycobacterium avium* Dihydrofolate Reductase," J. Med. Chem., 2004, vol. 47, No. 10, pp. 2475-2485.*

* cited by examiner

*Primary Examiner* — Shafiqul Haq
*Assistant Examiner* — Galina Yakovleva
(74) *Attorney, Agent, or Firm* — Seed IP Law Group PLLC

(57) ABSTRACT

The present disclosure is directed to antibodies specific to carbamazepine, immunogens used to produce the antibodies, and immunoassay kits and methods for using the antibodies.

3 Claims, 2 Drawing Sheets

ANTIBODIES SPECIFIC TO CARBAMAZEPINE

BACKGROUND

1. Technical Field

The present disclosure is directed to antibodies specific to carbamazepine, immunogens used to produce the antibodies, and immunoassay kits and methods for using the antibodies.

2. Description of the Related Art

Carbamazepine (5H-dibenzo[b,f]azepine-5-carboxamide) is an anticonvulsant and mood stabilizing drug used primarily in the treatment of epilepsy, bipolar disorder, and trigeminal neuralgia. Because of side effects of this drug, including life-threatening allergic reactions and toxic epidermal necrolysis that may cause severe damage to the skin and internal organs, it is important to monitor the levels of the drug in the patient's serum during treatment.

Immunoassays using antibodies specific to carbamazepine have been used in detecting and monitoring the levels of carbamazepine in patients' serum. Known antibodies are typically produced using immunogens in which immunogenic carriers are linked to the amido group of carbamazepine due to the relative easiness in derivatizing at this position. However, antibodies produced with this derivatization are generally not very sensitive.

BRIEF SUMMARY

The present disclosure provides antibodies specific to carbamazepine, immunogens used to produce the antibodies, and immunoassay kits and methods for using the antibodies.

In one aspect, the present disclosure provides an immunogen having the structure:

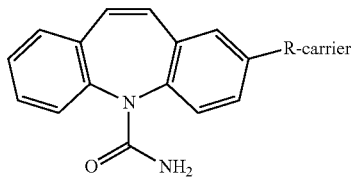

wherein the carrier is an immunogenic carrier material, and wherein R is a linkage.

In certain embodiment, the immunogenic carrier is a protein.

In certain embodiment, R is a linking group, such as —O—$(CH_2)_n$—COO— in which n is an integer between 0 to about 1,000. In certain embodiment, R is —O—$(CH_2)_4$—COO—.

In another aspect, the present disclosure provides an antibody prepared against the immunogen provided herein.

In another aspect, the present disclosure provides an immunoassay reagent comprising the antibody prepared against the immunogen provided herein.

In another aspect, the present disclosure provides an immunoassay kit, comprising: (1) an antibody having binding specificity for carbamazepine; and (2) one or more reagents for detecting a complex of the antibody and carbamazepine, wherein the antibody is obtained using an immunogen provided herein.

In certain embodiments, the reagents comprise a reagent selected from the group consisting of an enzyme, a radioisotope, a fluorescent reagent, a luminescent reagent and a chemiluminescent reagent.

In certain embodiments, the reagents comprise an enzyme-carbamazepine conjugate and a substrate for the enzyme.

In certain embodiment, the antibody is bound to a solid surface, and said reagents comprise an enzyme-carbamazepine conjugate.

In another aspect, the present disclosure provides a method for producing an antibody specific to carbamazepine, comprising: (a) injecting an animal with the immunogen provided herein, and (b) collecting an antibody produced by the animal in response to the immunogen.

In another aspect, the present disclosure provides a method for determining the presence or absence of carbamazepine in a sample, comprising: (a) exposing a sample to an antibody specific to carbamazepine, the antibody being prepared against the immunogen provided herein, and (b) determining the presence or absence of the binding between the antibody and the contents of the sample, wherein the presence or absence of the binding indicates the presence or absence of carbamazepine in the sample, respectively.

In certain embodiment, the immunogenic carrier is a protein.

In certain embodiment, R is a linking group, such as —O—$(CH_2)_n$—COO— in which n is an integer between 0 to about 1,000. In certain embodiment, R is —O—$(CH_2)_4$—COO—.

In certain embodiments, step (b) comprises performing an enzyme immunoassay, such as a homogenous enzyme immunoassay or ELISA.

In certain embodiments, the sample is a physiological sample, such as a blood sample.

In a related aspect, the present disclosure provides a method for determining the concentration of carbamazepine in a sample, comprising: (a) exposing a sample to an antibody specific to carbamazepine, the antibody being prepared against the immunogen provided herein, and (b) determining the concentration of carbamazepine in the sample by measuring the binding between the antibody and the contents of the sample.

In certain embodiment, the immunogenic carrier is a protein.

In certain embodiment, R is a linking group, such as —O—$(CH_2)_n$—COO— in which n is an integer between 0 to about 1,000. In certain embodiment, R is —O—$(CH_2)_4$—COO—.

In certain embodiments, step (b) comprises performing an enzyme immunoassay, such as homogenous enzyme immunoassay.

In certain embodiments, the sample is a physiological sample, such as a blood sample.

DETAILED DESCRIPTION

Figure 1:
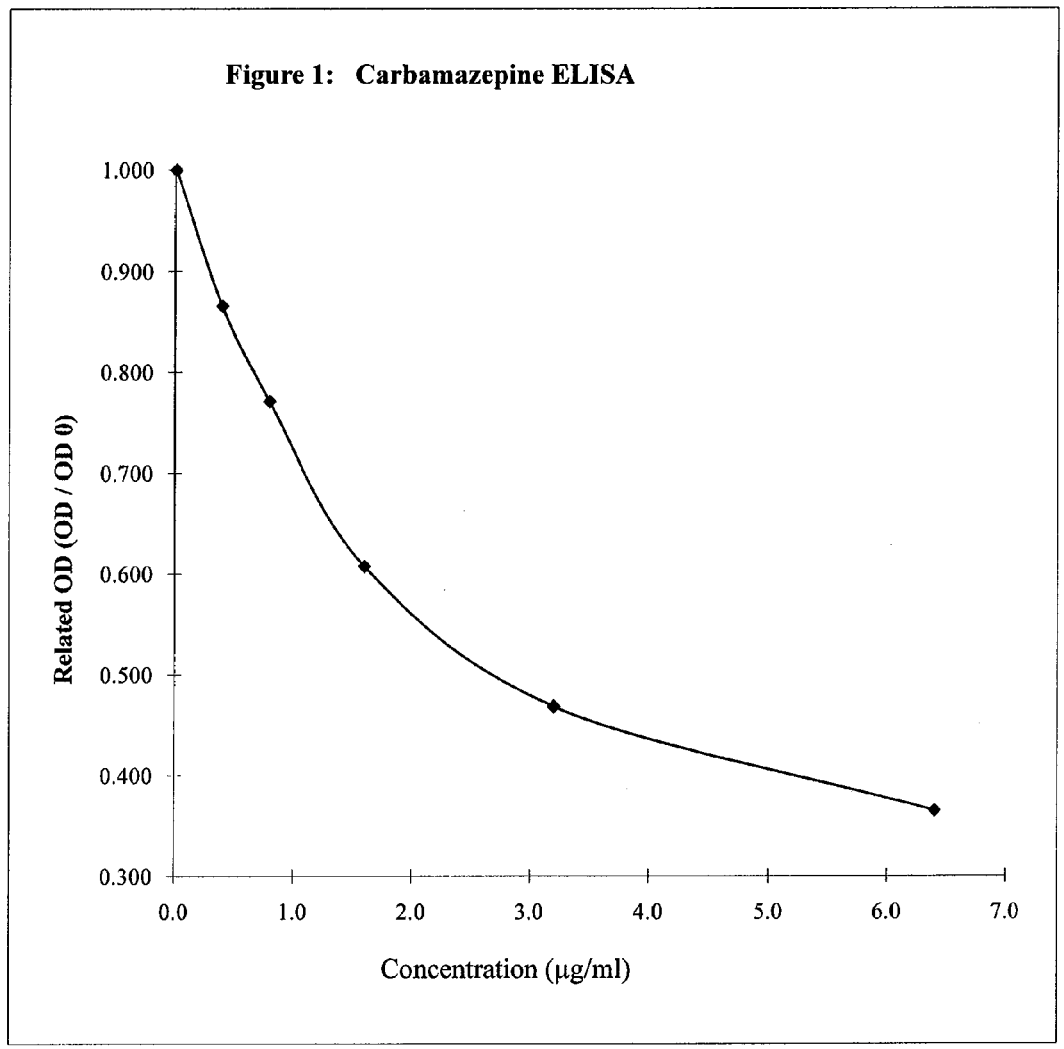
FIG. 1 shows a dose response curve of a carbamazepine ELISA assay.

The present disclosure provides antibodies specific to carbamazepine, immunogens used to produce the antibodies, and immunoassay kits and methods for using the antibodies. Unlike previously known immunogens, the immunogens provided by the present disclosure are derived from carbamazepine derivatives that retain the amido group of carbamazepine. Antibodies produced using the immunogens provided herein bind to carbamazepine with high affinities and thus allow for the development of highly sensitive and specific immunoassays for detecting carbamazepine.

The immunogen of the present disclosure has the following structure:

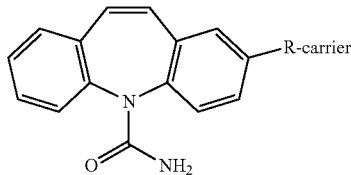

wherein carrier is an immunogenic carrier, and R is a linkage.

The carbamazepine may be coupled to the immunogenic carrier through linkage R by any techniques known in the art or hereafter developed. Linkage R is preferably a linking group capable of linking carbamazepine to the carrier. Preferably, linkage R is —O—$CH_2)_n$COO—, wherein n is an integer from 0 to many. The value for n can be any number that will maintain the functionality of the linking group. Preferably, n is between 0 and about 1000, more preferably is between 0 and about 100, and most preferably is between 0 and about 10. Most preferably R is —O—$(CH_2)_4$COO—. Alternatively, R may be a linking group of —$(CH_2)_n$—COO—, —CO—$(CH_2)_n$—COO—, NH—$(CH_2)_n$—COO—, where n is 1 to many (e.g., 1 to 1000, 1 to 100, or 1 to 10); or R may be a direct linkage between carbamazepine and the immunogenic carrier.

The immunogenic carrier can be any immunogenic carrier known in the art or hereafter developed. Preferably, the immunogenic carrier will be a protein or polypeptide; most preferably a protein, although other materials of sufficient size and immunogenicity can be used. Particularly preferred immunogenic carriers include albumin, hemocyanin (KLH), and thyroglobulin.

The immunogen of the present disclosure is used to produce an antibody specific to carbamazepine. It should be understood that as used herein, the term antibody refers not only to the complete antibody, but also to antibody fragments or derivatives, provided the binding properties of the complete antibody are maintained.

Antibodies of the present disclosure have binding specificity for carbamazepine. It should be understood that an antibody is considered specific to carbamazepine although it may have some binding affinity for non-carbamazepine compounds, provided the affinity for carbamazepine is measurably higher than the affinity for non-carbamazepine compounds. For example, an antibody is considered specific to carbamazepine if, at a specified analytical cut off point for an assay, the antibody will produce a positive test result for carbamazepine, but will not produce a positive result for samples which do not contain carbamazepine, but may contain other drug compounds.

Antibodies of the present disclosure may be produced using the immunogen disclosed herein via conventional techniques known in the art or hereafter developed. Antibodies of the present disclosure may be polyclonal or monoclonal and preferably are polyclonal. Thus, when used herein, the term "an antibody" would encompass a polyclonal antibody comprising multiple antibody species. Polyclonal antibodies are typically formed by inoculating a host animal, such as a rabbit, goat, mouse, sheep, guinea pig or horse, at one or more sites with an immunogen, either alone or in combination with an adjuvant. Subsequent injections are made until the optimal titer is reached. The animal is bled to yield a suitable volume of specific antiserum, which may be purified. Monoclonal antibodies may be produced by somatic cell hybridization techniques, also well known in the art.

The present disclosure is also directed to immunoassays using an antibody disclosed herein to detect carbamazepine in a sample. Antibodies of the present disclosure may be used in any immunoassays known or hereafter developed, such as a radioimmunoassay (RIA), a fluoroimmunoassay, and a gold labeled strip. The immunoassays of the present disclosure are preferably an enzyme immunoassay. Any enzyme immunoassay known in the art or hereafter developed may be used consistent with the present disclosure, such as an ELISA, and an EMIT.

The immunoassay may comprise exposing a sample to be tested to the antibody disclosed herein, and determining the presence or absence of the binding of the antibody to the contents of the sample. If the antibody binds to the contents of the sample, it is an indication that the sample contains carbamazepine. Preferably, the test is performed in vitro. The sample is preferably a fluid sample, more preferably a physiological sample, and most preferably a blood sample. The method may also comprise the testing of positive and negative control samples. The immunoassay methods of the present disclosure (e.g., a gold strip assay) may be used as a qualitative test to detect the presence of carbamazepine. Alternatively, the immunoassay methods of the present disclosure are quantitative tests that may be used to measure carbamazepine levels in samples (e.g., patients' serum). For example, the immunoassay may comprise exposing a sample to be tested to the antibody disclosed herein, and determining the concentration of carbamazepine in the sample by measuring the binding of the antibody to the contents of the sample (e.g., EMIT). The immunoassay provided herein may be performed manually or utilizing an automated machine. If an automated machine is used, the method may further comprise calibrating the machine.

In a preferred embodiment, the immunoassay of the present disclosure is used in an ELISA, EMIT or gold labeled strip test. In one type of ELISA (enzyme-linked immunosorbent assay), the sample to be tested is combined with an enzyme-carbamazepine conjugate and run over a surface to which immobilized antibodies of the present disclosure have been attached. Carbamazepine in the sample competes with the enzyme-carbamazepine conjugate to bind to the antibody layer. The enzyme-carbamazepine conjugate bound to the antibody layer can be visualized by the addition of a substrate to the enzyme that changes color in the presence of the enzyme. Free carbamazepine in the sample results in fewer enzyme-carbamazepine conjugates bound to the antibody, which results in a smaller color change. The enzyme may be any enzyme known in the art or hereafter developed suitable for use in ELISA. Preferably the enzyme is horseradish peroxidase (HRP).

An EMIT (enzyme multiplied immunoassay) is a homogeneous immunoassay, based on the competition between the free carbamazepine in the sample and carbamazepine conjugated to an enzyme for the binding sites of the anti-carbamazepine antibodies. The enzyme is conjugated to carbamazepine that is recognized by the antibody. The enzyme may be any enzyme known in the art or hereafter developed suitable for use in EMIT assays. Preferably, the carbamazepine is conjugated to Glucose-6-Phospahte Dehydrogenase ("G6PDH"). G6PDH converts glucose-6-phosphate (G6P) and oxidized nicotinamide adenine dinucleotide ($NAD^+$) to gluconate-6-phosphate and NADH, respectively. This process results in a change in absorbance, or a signal, measured at 340 nm. The enzyme-carbamazepine conjugate in the reagent is constituted in such a way that, as soon as the antibody of the present disclosure binds to the enzyme-carbamazepine conjugate, the enzyme activity is inhibited. The carbamazepine present in the sample competes with the conjugated carbamazepine to bind to the antibody. Thus, if there is more carbamazepine in the sample, there is more free enzyme-carbamazepine conjugate and a stronger signal is produced.

Preferably, the method of the present disclosure is performed using an immunoassay kit. The immunoassay kit comprises an antibody disclosed herein or a reagent that comprises the antibody disclosed herein and may further comprise one, multiple or all elements needed to perform the desired immunoassay. Preferably the kit comprises one or more reagents for detecting a complex of the antibody and carbamazepine. The reagents may be any reagents known in the art. Preferably the reagents are selected from the group consisting of an enzyme, a radioisotope, a fluorescent reagent, a luminescent reagent and a chemiluminescent reagent. A kit for performing EMITs would preferably include an antibody disclosed herein, an enzyme-carbamazepine conjugate, and a substrate. In the preferred embodiment, the enzyme is G6PDH, and the substrate is G6P. In such an embodiment, preferably the antibody and substrate are packaged as a first reagent, and the enzyme-carbamazepine conjugate is packaged as a second reagent. Preferably the first reagent also contains $NAD^+$. A kit for performing ELISAs preferably includes a solid surface, such as beads, to which an antibody disclosed herein is affixed, as well as a reagent comprising an enzyme-carbamazepine conjugate. Additional buffers and components may be added to the reagents, as may be known in the art or hereafter developed. The kit may also include controls, preferably positive and negative controls, and a calibrator.

The immunoassays provided herein can be used for monitoring the levels of carbamazepine in patients' blood sample (e.g., serum). Such monitoring is important to determine the optimal amount of carbamazepine (e.g., an effective amount without causing severe side effects) for individual patients and to adjust the amount during treatment.

EXAMPLES

Example 1

Preparation of Carbamazepine Derivative

This example describes the preparation of an exemplary carbamazepine derivative having the structure:

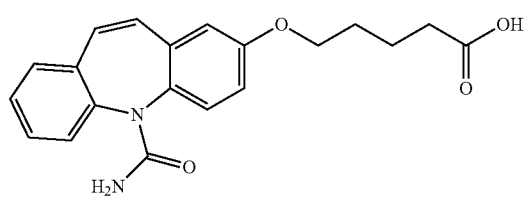

Carbamazepine Derivative

The synthetic route is shown below:

Scheme 1:

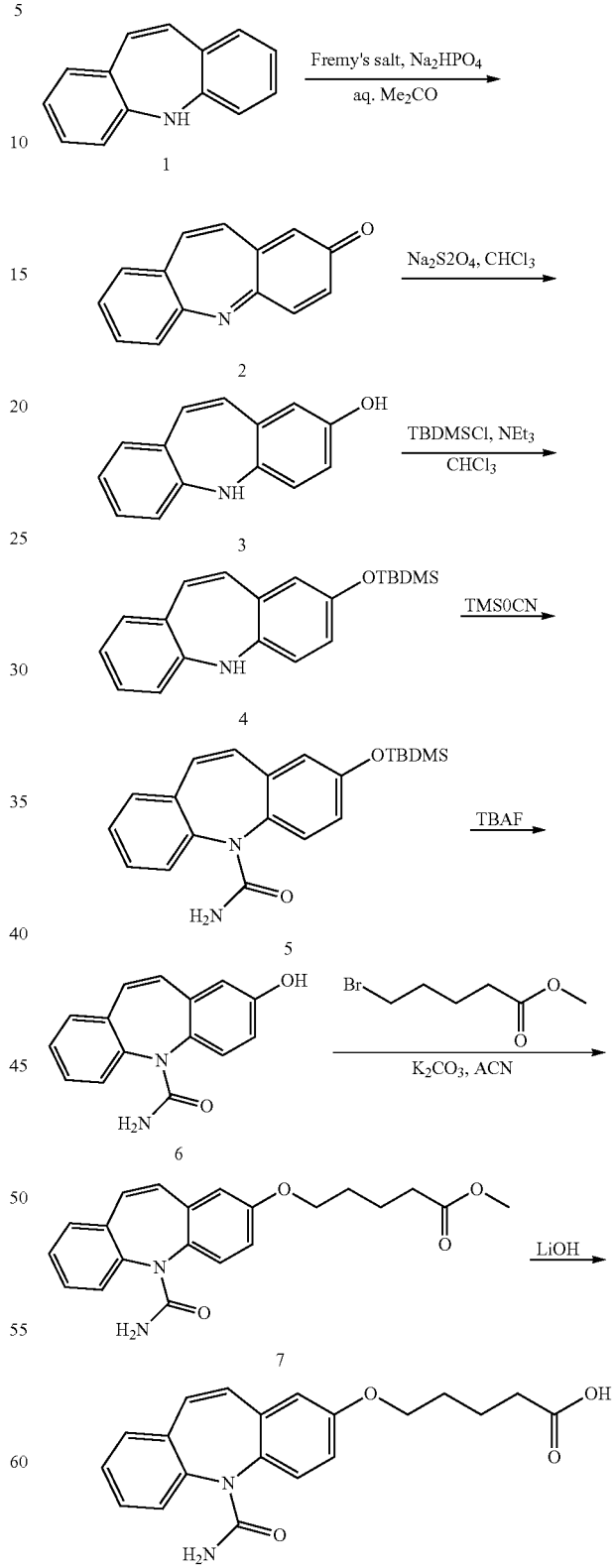

Carbamazepine Derivative

1. Synthesis of Compound 2:

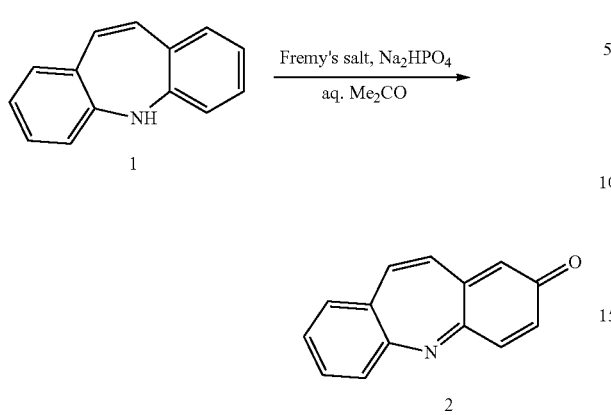

A solution (KSO$_3$)$_2$NO (Fremy's salt, 2.5 g, 9.32 mmol) was added in small portions to a solution of Na$_2$HPO$_2$ (1.8 g, 12.7 mmol) in double-distilled H$_2$O (95 mL), and the pH was adjusted to exactly 7.22 with a meter. Small portions of the purple solution were then added to a vigorously stirred solution of compound 1 (0.55 g, 2.76 mmol) in acetone (60 mL) and after 10 min the mixture was filtered and left in the refrigerator overnight. After concentration to a small volume by rotary evaporation under a stream of argon, the product was extracted into Et$_2$O (500 mL). The solvent was evaporated and the residue was purified by flash chromatography on silica gel using a 4:1 mixture of hexanes and Teac as the eluent. A deep-red microcrystalline powder after re-crystallization from Et$_2$O was the desired iminoquinone 2 (0.12 g, 21%) as a red solid.

2. Synthesis of Compound 3:

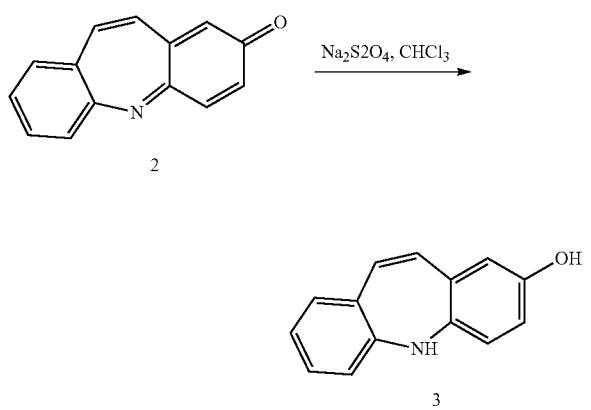

A solution of compound 2 (1.2 g, 5.8 mmol) in CHCl$_3$ (50 mL) was shaken in a separatory funnel with freshly prepared solution containing an excess of Na$_2$S$_2$O$_4$ (2.5 g, 14.3 mmol) in H$_2$O (20 mL) until the color of the organic layer changed from red to yellow. The aqueous layer was extracted with CHCl$_3$, the combined organic extracts were dried (Na$_2$SO$_4$), and the solvent was evaporated by rotary distillation. Re-crystallization of the residue from CHCl$_3$ afforded compound 3 as pale greenish-yellow crystals (1.1 g, 92%);

3. Synthesis of Compound 4:

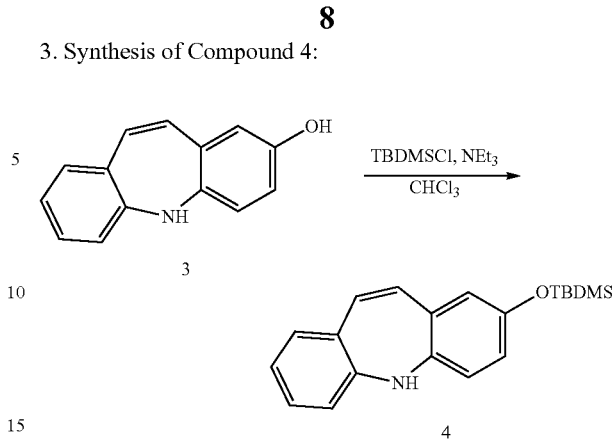

To the solution of compound 3 (1.1 g, 5.3 mmol) and 1 mL of TEA in 10 mL of CHCl$_3$, TBDMSCI (2 g, 15.2 mmol) was added, and the reaction mixture was stirred at room temperature for 3 days. The solvent was then evaporated. Water was added, and the resulting mixture was extracted with CHCl$_3$. The combined organic extracts were dried (Na$_2$SO$_4$), and the solvent was evaporated by rotary distillation. The above process gave 1.6 g of crude compound 4 without further purification.

4. Synthesis of Compound 5:

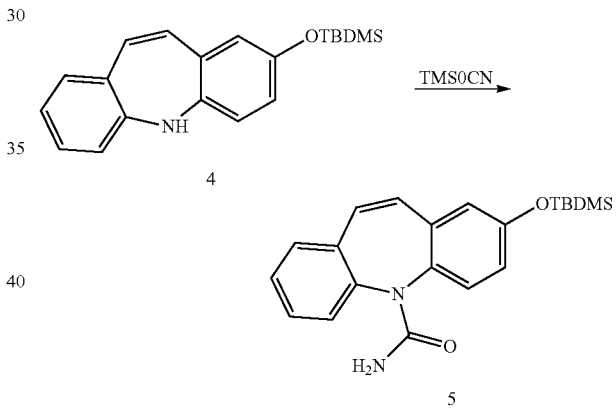

A mixture of compound 4 (1.6 g, 4.95 mmol) and 2 mL of TMSOCN in 10 mL of CHCl$_3$ was stirred at room temperature for 2 days. The solvent was evaporated. Water was added, and the mixture was extracted with CHCl$_3$. The combined organic extracts were washed with brine and dried over Na$_2$SO$_4$, and the solvent was evaporated by rotary distillation. The above process gave 1.6 g of crude compound 5 as a yellow solid.

5. Synthesis of Compound 6:

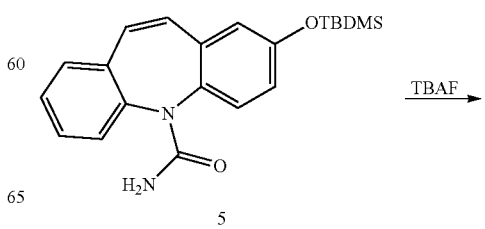

-continued

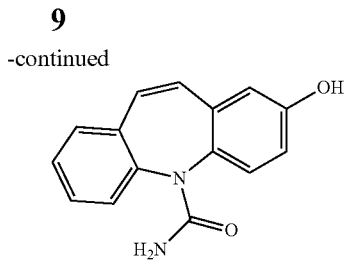

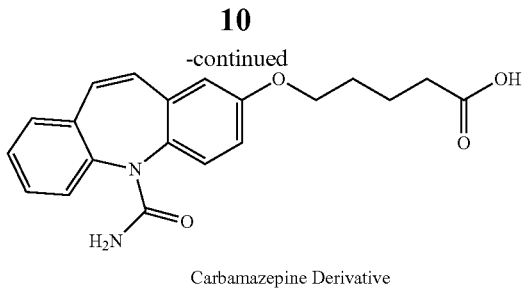

Carbamazepine Derivative

To the solution of compound 5 (1.6 g, 4.37 mmol) in 20 mL of THF, the solution of TBAF in THF (2 g, 15.2 mmol) was added. The mixture reaction was stirred at room temperature for 4 hrs. The solvent was evaporated. Water was added, and the mixture was extracted with EA. The combined organic extracts were dried ($Na_2SO_4$), and the solvent was evaporated by rotary distillation. After the crude compound was purified by chromatography (EA/PE=1:1), 1.0 g of compound 6 was obtained (Yield from compound 3 to compound 6: 75%).

6. Synthesis of Compound 7:

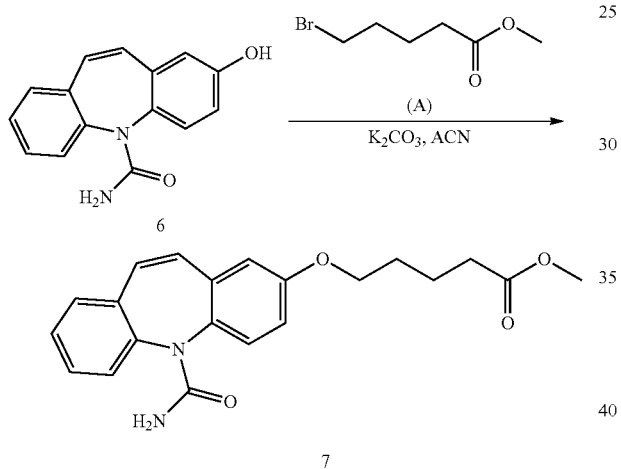

To a solution of compound 6 (1.0 g, 4.0 mmol) in 30 mL of ACN $K_2CO_3$ (1.38 g, 10.0 mmol) and compound A (1.16 g, 6.0 mmol) were added, and the solution was then stirred at room temperature overnight. The solution was filtered, concentrated under reduced pressure, and partitioned between water and EtOAc. The organic phase was dried over $Na_2SO_4$, filtered and concentrated under reduced pressure. The crude residue was purified by flash chromatography on silica gel (eluent: EA/PE=1/3) to give 1.1 g of compound 7 as white solid (Yield: 76%).

7. Synthesis of Carbamazepine Derivative:

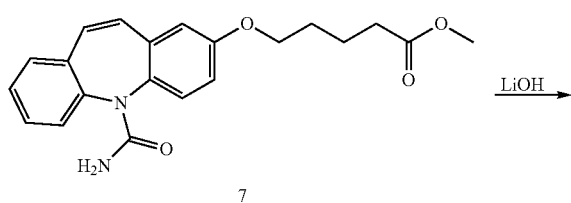

To the solution of compound 7 (1.1 g, 3.0 mmol) in 20 mL of THF, the solution of $LiOH.H_2O$ (0.48 g, 11.8 mmol) in 10 mL of $H_2O$ was added. After stirring for 6 hrs at 50° C., TLC indicated that the hydrolysis was over. The mixture was concentrated and acidified so that the water layer was about pH=3. The white solid was collected by filtration, and re-crystallized from MeOH to give 230 mg of Carbamazepine derivative as white solid (Yield: 48%).

$^1$H NMR spectra of the carbamazepine derivative were recorded on Bruker Avance III plus 400 MHz, and TMS was used as an internal standard. The results were: $^1$H NMR (DMSO-d6, 400 MHz): 12.04 (s, 1H), 7.37-7.45 (m, 3H), 7.29-7.35 (m, 2H), 5.53 (s, 1 H), 3.98 (t, 2H, J=6.4 Hz), 2.28 (t, 2H, J=7.2 Hz), 1.63-1.75 (m, 4H).

LCMS of the carbamazepine derivative was taken on a quadrupole Mass Spectrometer on Agilent LC/MSD 1200 Series (Column: Welchrom XB-C18 (50×4.6 mm, 5 μm) operating in ES (+) or (−) ionization mode; T=30° C.; Flow rate=1.5 mL/min. The results were: LCMS (mobile phase: 5%-60% Acetonitrile-Water): purity is 99.2%, Rt=2.769 min; MS Calcd.: 352; MS Found: 353 (M+1).

Example 2

Synthesis of the BSA-Carbamazepine Derivative Immunogen

An immunogen in which BSA is linked to carbamazepine via —O—$(CH_2)_4$—COO— was synthesized as follows:

Bovine Serum Albumin (BSA) (200 mg) was dissolved in 50 ml 0.2 M phosphate buffer, pH 8.5. The following chemicals were added to a small beaker and stirred to dissolve: 200 mg Carbamazepine derivative as prepared in Example 1, 3.5 ml dimethylformamide (DMF), 3.5 ml Reagent Alcohol, 7.0 ml 10 mM Potassium Phosphate Buffer, pH 5.0, 200 mg of 1-Ethyl-3-(-3-Dimethylaminopropyl)Carbodiimide, and 50 mg Sulfo-NHS (N-hydroxysuccinimide). The mixture was stirred for reaction at room temperature for 30 minutes. The resulting solution was added dropwise to the BSA solution and stirred overnight at 2-8° C. The conjugated immunogen was purified by dialysis.

Example 3

Antibody Production

Production of the antibodies of the present disclosure was performed with conventional methods. In brief, the immunogen as prepared in Example 2 was diluted to 1.0 mg/ml in phosphate buffered saline (PBS). 1.0 ml of the immunogen solution was injected into rabbits with complete Freunds adjuvant. After 2-3 weeks, the animal was injected with 1.0 ml of the same immunogen solution with incomplete Freunds adjuvant. The same injection was repeated every other week until acceptable titer was obtained.

Example 4

Carbamazepine ELISA Assay

The Carbamazepine ELISA was developed with the antibody generated from Example 3. This assay is a competitive micro-immunoassay for determination of carbamazepine in a fluid sample. Carbamazepine in the fluid sample and carbamazepine derivative linked with the enzyme (HRP)-conjugate compete for the finite sites of the antibody coated on the solid surface of the microwell. If little or no carbamazepine is present in the fluid sample, more enzyme labeled carbamazepine derivative will bind to the antibody on the solid surface. Conversely, if a large or a significant amount of carbamazepine is present in the fluid sample, less enzyme labeled carbamazepine derivative will bind to the antibody, producing less color signal. The absorbance produced is inversely proportional to the amount of carbamazepine in the fluid sample.

The assay using the antibody generated from Example 3 produced the dose response curve as shown in FIG. 1.

Example 5

Carbamazepine Homogenous Immunoassay

The carbamazepine EMIT (Enzyme Multiplied Immunoassay Technique) was developed with the antibody generated from Example 3. This assay is a competitive assay in which the antibody bound carbamazepine and free carbamazepine are not separated via immobilization. The assay is based on the competition between the free carbamazepine in a fluid sample and carbamazepine derivative bound to an enzyme Glucose-6-Phosphate Dehydrogenase [G6PDH] for specific antibody binding sites. The carbamazepine present in a fluid sample competitively displaces the enzyme-bound carbamazepine derivative and frees it from the antibody, thus making the enzyme active again. Thus, the more carbamazepine in a fluid, the more freed carbamazepine derivative-G6PDH conjugate, and the higher the signal.

Figure 2:
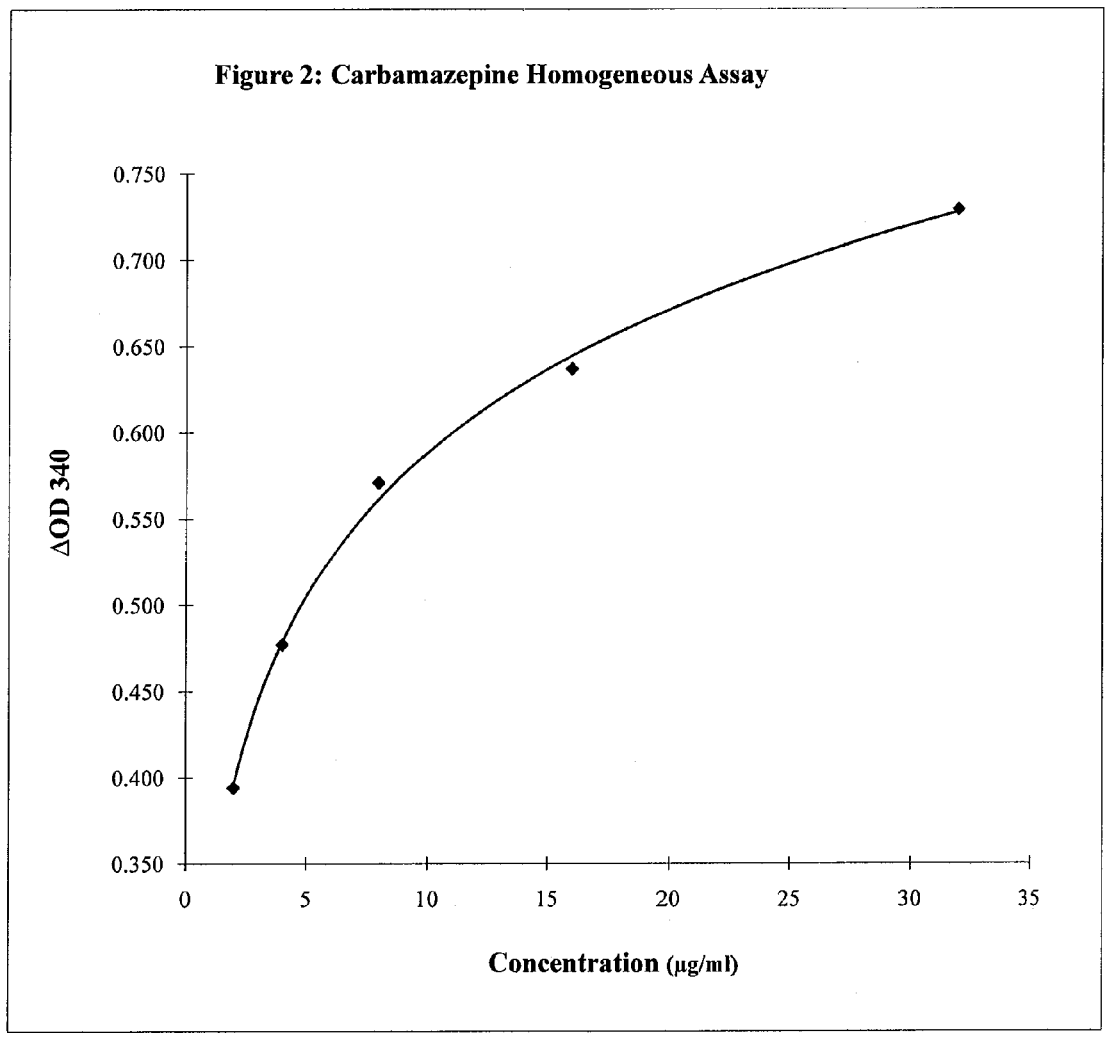
FIG. 2 shows a dose response curve of a carbamazepine homogenous immunoassay.

The assay in this disclosure produced the dose response curve (FIG. 2).

Example 6

Interference from Other Drugs

Interference from other drugs was tested using 30 frequently used chemicals and medicines, at concentrations of 10.0 μg/ml. The results of the chemicals tested are listed in the following table:

| ID# | Chemical Name | Equivalent Carbamazepine Conc. (μg/ml) |
|---|---|---|
| 1 | Acetylsalicylic Acid | <0.1 |
| 2 | Amobarbital | <0.1 |
| 3 | Ampicillin | <0.1 |
| 4 | beta-Phenylethylamine | <0.1 |
| 5 | Caffeine | <0.1 |
| 6 | Chlordiazepoxide | <0.1 |
| 7 | Chlorpromazine | <0.1 |
| 8 | Clorazepate | <0.1 |
| 9 | d-Methamphetamine | <0.1 |
| 10 | Fenoprofen | <0.1 |
| 11 | Gemfibrozil | <0.1 |

-continued

| ID# | Chemical Name | Equivalent Carbamazepine Conc. (μg/ml) |
|---|---|---|
| 12 | Gentisic Acid | <0.1 |
| 13 | Hydrocodone | <0.1 |
| 14 | Ibuprofen | <0.1 |
| 15 | Imipramine | <0.1 |
| 16 | (L)-Ephedrine | <0.1 |
| 17 | Lidocaine | <0.1 |
| 18 | Naproxen | <0.1 |
| 19 | Niacinamide | <0.1 |
| 20 | Penicillin | <0.1 |
| 21 | Phenylephrine | <0.1 |
| 22 | Phenylpropanolamine | <0.1 |
| 23 | Procainamide | <0.1 |
| 24 | Procaine | <0.1 |
| 25 | Quinidine | <0.1 |
| 26 | Zomepirac | <0.1 |
| 27 | Ecgonine Methyl Ester | <0.1 |
| 28 | Ecgonine | <0.1 |
| 29 | Diazepam | <0.1 |
| 30 | (−)-Cotinine | <0.1 |

The samples were tested in duplicate, following the procedures used in Example 4. All 30 samples produced a negative test result. Thus, the immunoassay of the present disclosure is specific to carbamazepine.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An immunogen having the structure:

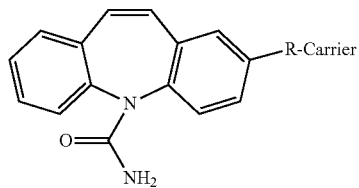

wherein the carrier is an immunogenic carrier material, and wherein R is —O—$(CH_2)_4$—CO—.

2. The immuogen of claim 1, wherein the immunogenic carrier is a protein.

3. A method for producing an antibody specific to carbamazepine, comprising:
   injecting an animal with the immunogen of claim 1,
   collecting an antibody produced by the animal in response to the immunogen.

* * * * *